United States Patent [19]

Trivedi

[11] 4,104,478
[45] Aug. 1, 1978

[54] CATALYTIC HYDROGENATION OF FATTY ACIDS

[75] Inventor: Bhupendra C. Trivedi, Columbus, Ohio

[73] Assignee: Ashland Oil, Inc., Ashland, Ky.

[21] Appl. No.: 854,441

[22] Filed: Nov. 23, 1977

[51] Int. Cl.$^2$ .............................................. C07C 29/00
[52] U.S. Cl. ..................................... 568/885; 252/472
[58] Field of Search ..................................... 210/638 A

[56] References Cited

U.S. PATENT DOCUMENTS

| | | | |
|---|---|---|---|
| 3,736,265 | 5/1973 | Suggitt | 260/638 A |
| 3,947,563 | 3/1976 | Dougherty | 260/638 A |

OTHER PUBLICATIONS

Brosdbent et al., "J. Org. Chem.", vol. 24 (1959), pp. 1847–1854.
Davenport et al., "Industrial and Engineering Chemistry", vol. 60, No. 11, (Nov. 1968), pp. 10–19.

*Primary Examiner*—Joseph E. Evans
*Attorney, Agent, or Firm*—William Kammerer

[57] ABSTRACT

A fatty acid is converted to the corresponding carbon length alcohol by the liquid phase hydrogenation of the carboxylic acid in the presence of a co-catalyst system consisting essentially of activated rhenium metal in combination with an extrinsic metal catalyst in the form of one of the platinum metals.

10 Claims, No Drawings

CATALYTIC HYDROGENATION OF FATTY ACIDS

BACKGROUND OF THE INVENTION

1. Field of the Invention

This invention relates to a process for the catalytic hydrogenation of a fatty acid.

2. Description of the Prior Art

Fatty alcohols, particularly the higher alcohols, are important commodities in the chemical industry whose uses as such and as intermediates are legion. The bulk of the fatty alcohols commercially available at present are producted synthetically either by the OXO process or in accordance with Ziegler chemistry. These methods employ the higher terminal olefins and ethylene, respectively, as the primary feed stocks. Since these feed stocks are petroleum derived, their costs have mounted so considerably of late that renewed interest is currently being focused on the reductive conversion of fatty acids to the corresponding alcohols which to date has only been used to produce certain specialty alcohols not available by the indicated synthetic routes.

The persistent problem with the method for the catalytic hydrogenation of a fatty acid to the alcohol is that the processing conditions involved in terms of temperature and pressure, particularly the latter, are exceedingly strenuous. The source of this problem resides in the catalyst itself. For years attention has been principally directed toward enhancing the catalytic activity of copper values for this purpose. More recently, however, rhenium has been proposed as an effective catalyst requiring less strenuous processing conditions than the more effective copper catalysts which had hitherto been developed. The supporting published data in respect of this finding are noteworthy and are reported by H. Smith Broadbent et al. in *J. Org. Chem.*, 24, 1847 (1959).

As acknowledged, rhenium itself is quite effective as a catalyst in carrying out the indicated hydrogenation method under acceptably tolerable pressure conditions. Beyond this, however, rhenium results in excellent selectivity toward the formation of the desired product. Notwithstanding the foregoing, improvement of the catalyst's capability to provide higher yield conversion levels is desirably called for. Accordingly, the foremost objective of this invention is to enhance the catalytic activity of rhenium metal in a manner whereby improved conversion yields are realized as compared with the use of said catalyst alone.

SUMMARY OF THE INVENTION

In accordance with the present invention, the catalytic effectiveness of activated rhenium metal for the conversion of a fatty acid to the corresponding carbon length alcohol by hydrogenation is enhanced through the use of said metal in combination with an extrinsic catalyst selected from the group consisting of ruthenium, rhodium, platinum and palladium. The extrinsic catalyst component in the co-catalyst systems contemplated herein constitute from 20–60% of the total weight of the combination as opposed to using trace amounts thereof for promoting purposes.

DESCRIPTION OF THE PREFERRED EMBODIMENTS

The active rhenium metal, referred to as rhenium black, can most conveniently be obtained by the reduction of rhenium heptoxide. In context of the present invention, there are two ways suitable for generating rhenium black. The preference for one or the other of these alternatives essentially turns on the method contemplated for carrying out the hydrogenation reaction; i.e., either by batch or continuous processing. In accordance with batch processing, it is preferred to generate rhenium black in situ by hydrogenating rhenium heptoxide in solution in the presence of the indicated extrinsic catalyst and the acid sought to be reduced through the agency of the catalyst system. The extrinsic metal catalyst is availed of in its commercially available form as 5% metal supported on carbon in accordance with this alternative.

In the continuous processing mode, the rhenium black is most advantageously prepared ex situ; i.e., out of site of the fatty acid subsequently to be reduced by the catalyst. Likewise, it is preferred in this instance to prepare rhenium black along with the catalytically active form of the extrinsic metal catalyst so as to provide the co-catalyst system supported on a common support. This is readily accomplished by adding aqueous solutions of applicable salts of the respective metals to silica gel. The gel-containing mixture is then dehydrated by heating to about 400° C. and holding for several hours in the presence of hydrogen in order to convert the metals to their catalytically active state.

As pointed out hereinabove, the extrinsic metal catalyst component of the co-catalyst systems useful in the practice of this invention include ruthenium, rhodium, platinum and palladium. The extrinsic metal catalyst is present in combination with the rhenium black in the weight ratio of 0.25–1.5 parts thereof per part of the latter. Most preferably, the weight ratio of rhenium black to the extrinsic metal catalyst is 1:(0.5–1.0), respectively.

The reduction reaction is carried out in the liquid phase. In accordance with batch processing, the acid substrate is preferably present in solution in a polar solvent. The applicable broad reaction temperature range of from 170°–250° C. is accordingly compatible with the liquid phase processing employing any of the $C_4$–$C_{24}$ fatty acids contemplated therein. More preferably, the reaction temperature is in the order of from 200°–230° C. Representative polar solvents include the lower alkanols and 1,4-dioxane with the latter being particularly suitable for the purpose at hand. The acid and the solvent when employed are present preferably on about an equal weight basis. Also, it is advantageous to have present a minor amount of water in the reaction mixture. The presence of water serves to favor the conversion of the acid to alcohol directly and thus minimizes the formation of ester derivatives in the product mix. A suitable amount of water is from about 10–30% based on the weight of the solvent present in the reaction mixture.

As previously mentioned, excellent selectivity toward the formation of desired products (alcohol and ester derivatives) is provided by the use of rhenium black as the hydrogenation catalyst. The practice of the present invention, on the other hand, results in the main in improved conversion yields compared to the use of rhenium black alone under comparable hydrogen concentration. In this connection, maximum conversion yields are to be realized with the use of a hydrogen pressure in the range of 140–170 atmospheres. On the other hand, hydrogen pressure in the range of 20–70 atmospheres results in a conversion yield comparable to that obtained with rhenium alone at substantially higher pressures. Since the conversion and selectivity values are important criteria in evaluating the effectiveness of the hydrogenation catalyst for the purpose contemplated herein, the definitions thereof are warranted and such are given as follows:

% Conversion = 100 − (%Acid + 0.5624 × %Ester)

$$\% \text{ Selectivity} = \frac{\text{Alcohol} + 0.5078 \times \text{Ester}}{\text{Total Product Component}}$$

The following examples are given to illustrate the practical implementation of the present invention and to set forth the best mode contemplated for carrying out the invention.

EXAMPLE I

Into a 300 ml Magnedrive autoclave were charged 28.8 g (0.2 mole) octanoic acid, 28.8 g 1,4-dioxane, 5.0 g water, 0.13 g (0.3 mmoles) rhenium heptoxide and 1.0 g of 5% ruthenium on carbon (20% wet). The reactor was flushed 3 times with 1000 psi hydrogen while stirring. The reactor was pressurized to 2000 psi and heated at 170° ± 3° C. for three hours at which time only a trace of acid was found unreacted by GLC. The results obtained are reported as Run No. 1 in the following Table I. The results on Run Nos. 2–10 are likewise tabulated in Table I. The latter runs were conducted in the identical fashion as for Run No. 1 but varying processing parameters as indicated in the Table. Product yield in all instances was determined by GLC.

TABLE I

| Run | Catalyst(g. atom) Rhenium | Extrinsic (Me) | Temp. (° C.) | Pressure (atm.) | Time (hrs.) | % Conver. | % Select. |
|---|---|---|---|---|---|---|---|
| 1 | $5.37 \times 10^{-4}$ | $4 \times 10^{-4}$(Ru) | 170 | 170 | 3 | 91.0 | 100.0 |
| 2 | " | " (Rh) | " | " | ~6 | 84.3 | ~100.0 |
| 3 | " | " (Pd) | " | " | 5 | 79.9 | 71.9 |
| 4 | " | " (Pt) | " | " | 5 | 74.6 | 86.2 |
| 5 | $10.74 \times 10^{-4}$ | NONE | " | " | 5 | 54.1 | 100.0 |
| 6 | $5.37 \times 10^{-4}$ | $4 \times 10^{-4}$(Pd) | 200 | 34 | 5 | 31.0 | 100.0 |
| 7 | " | $8 \times 10^{-4}$(Pd) | " | " | 5 | 44.0 | 94.8 |
| 8 | $10.74 \times 10^{-4}$ | " | " | " | 5 | 50.9 | 94.9 |
| 9 | $5.37 \times 10^{-4}$ | $16 \times 10^{-4}$(Pd) | " | " | 5 | 42.3 | 80 |
| 10* | " | $4 \times 10^{-4}$(Ru) | 230 | 1.0 | 3 | 23.3 | 40.1** |

*Lauric acid (0.2 mole)
**Remaining product hydrocarbon

EXAMPLE II

The purpose of this example is to illustrate the reductive conversion of octanoic acid to octanol in accordance with the invention by a continuous processing procedure. The reactor was in the form of a ½-inch SS tube of 12-inch length having a capacity of about 18 ml. The catalyst system residing in the reactor was that of rhenium in combination with palladium supported on silica, such having been prepared ex situ in the manner described hereinabove. Processing conditions maintained constant in the plurality of runs reported herein included a reaction temperature of 200° C., pressure of 20 atmospheres, an acid feed rate of 16–20 ml/hour and a hydrogen flow rate of 18–25 l/hour. Duration of each run was approximately 1 hour. Variations in the catalyst system observed in the respective runs together with the results obtained are set forth in the following Table II.

TABLE II

| Run No. | Wt. % Rhenium | Wt. % Palladium | % Conversion | % Selectivity |
|---|---|---|---|---|
| 11 | 4.73 | — | 10 | 83.6 |
| 12 | 4.64 | 2.32 | 38.6 | ~100.0 |
| 13 | 2.31 | 4.62 | 21.8 | 96.1 |
| 14 | 2.38 | 2.38 | 23.8 | 100.0 |
| 15 | 4.54 | 4.54 | 59.1 | 98.2 |

What is claimed is:

1. A process for the catalytic reduction of a $C_4$–$C_{24}$ fatty acid to the corresponding carbon length alcohol which comprises hydrogenating the fatty acid at a temperature of from about 170°–250° C. and at a pressure of from about 20–140 atmospheres in the presence of a catalytically effective amount of a co-catalyst system consisting essentially of 1 part by weight of activated rhenium and from 0.25–1.5 parts of an extrinsic metal catalyst selected from the group consisting of ruthenium, rhodium, platinum and palladium.

2. A process in accordance with claim 1 wherein said temperature is from 200°–230° C. and said pressure is from 20–70 atmospheres.

3. A process in accordance with claim 2 wherein the co-catalyst system consists essentially of 1 part by weight of rhenium and from 0.5–1.0 parts of said extrinsic metal catalyst.

4. A process in accordance with claim 3 wherein said fatty acid is a $C_8$–$C_{20}$ fatty acid.

5. A process in accordance with claim 4 wherein said extrinsic metal catalyst is ruthenium.

6. A process in accordance with claim 4 wherein said extrinsic metal catalyst is rhodium.

7. A process in accordance with claim 4 wherein said extrinsic metal catalyst is platinum.

8. A process in accordance with claim 4 wherein said extrinsic metal catalyst is palladium.

9. A process in accordance with claim 4 wherein said activated rhenium is generated in situ from rhenium heptoxide.

10. A process in accordance with claim 1 wherein said hydrogenation reaction is conducted in a continuous flow reactor containing said co-catalyst system prepared ex situ.

* * * * *